(12) United States Patent
Takahashi et al.

(10) Patent No.: US 6,337,050 B1
(45) Date of Patent: Jan. 8, 2002

(54) SAMPLE RACK HANDLING SYSTEM

(75) Inventors: Katsushi Takahashi; Hitoshi Tokieda; Toshiyuki Ikeda; Susumu Kai, all of Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/292,990

(22) Filed: Apr. 16, 1999

(30) Foreign Application Priority Data

Apr. 20, 1998 (JP) ............................................. 10-109722

(51) Int. Cl.[7] .......................... G01N 35/02; G01N 35/04
(52) U.S. Cl. .............................. 422/65; 422/63; 422/67; 422/68.1; 422/72; 436/43; 436/45; 436/47; 436/48; 436/49
(58) Field of Search .............................. 422/63, 65, 67, 422/68.1, 72; 436/43, 45, 47, 48, 49

(56) References Cited

U.S. PATENT DOCUMENTS

| | | | |
|---|---|---|---|
| 4,965,049 A | * 10/1990 | Lillig et al. | 422/68.1 |
| 5,008,082 A | * 4/1991 | Shaw | 422/65 |
| 5,055,408 A | * 10/1991 | Higo et al. | 436/48 |
| 5,207,986 A | * 5/1993 | Kadota et al. | 422/65 |
| 5,928,952 A | * 7/1999 | Hutchins et al. | 436/50 |
| 5,972,295 A | * 10/1999 | Hanawa et al. | 422/65 |
| 5,985,214 A | * 11/1999 | Stylli et al. | 422/65 |
| 6,019,945 A | * 2/2000 | Ohishi et al. | 422/65 |
| 6,060,022 A | * 5/2000 | Pang et al. | 422/65 |

FOREIGN PATENT DOCUMENTS

| | | |
|---|---|---|
| JP | 3-285175 | 12/1991 |
| JP | 11304810 A | * 11/1999 |
| WO | WO-9818009 A | * 4/1998 |

OTHER PUBLICATIONS

Total Clinical Laboratory Testing System for Laboratory Automation, Hitachi Review, vol. 41, No. 4, 1992, pp. 167–172.

* cited by examiner

*Primary Examiner*—Jill Warden
*Assistant Examiner*—Kathryn Bex
(74) *Attorney, Agent, or Firm*—Mattingly, Stanger & Malur, P.C.

(57) ABSTRACT

A rack transportation assembly having a projecting member projecting forward is fixed onto a floor by a plurality of adjusters so that its rack transportation surface is brought to a desired level. The projecting member has a first reference surface facing upward. A treatment unit structure having a rack transferring area has a second reference surface in its lower surface. The treatment unit structure is pushed toward the rack transportation assembly under a condition that the second reference surface is lifted upward using height-adjustable casters so as to not become higher than the first reference surface. Then, the treatment unit structure is lowered so that the second reference surface is mounted onto the first reference surface, and a height in the front side of the treatment unit structure is adjusted using the plurality of adjusters.

2 Claims, 5 Drawing Sheets

SAMPLE RACK HANDLING SYSTEM

BACKGROUND OF THE INVENTION

The present invention relates to a sample rack handling system and particularly to a sample rack handling system suitable for automatically performing pretreatment for sample inspection in a clinical inspection field.

An ordinary sample handling system comprises various kinds of treatment units (a centrifuge unit, a destoppler unit, an aliquoter unit, a bar-code labeler unit, a restoppler unit, a sorting unit, an analyzer unit and so on) respectively containing a rack transportation unit and transportation lines connecting between the treatment units, and the handling system is constructed by connecting between the treatment unit and the treatment unit, between the transportation line and the treatment unit, or between the transportation line and the transportation line.

An automatic sample handling system is proposed in "Hitachi Review, Vol.41, No.4, pages 167–172 (1992)". In the automatic sample handling system, a transportation line for transporting samples is composed of a plurality of transportation routes to branch the transportation line into a plurality of routes so that the samples may be distributed to the various kinds of treatment units.

The treatment units arranged in the system comprises an automatic centrifuge unit for separating blood into serum and cells, a destoppler unit for automatically removing a cap of a sample container, an aliquoter unit for pipetting serum from a mother sample container to a daughter sample container, a bar code labeler unit for attaching a bar code label having the same sample ID as that of the mother sample to the daughter sample container, a re-stoppler for setting the cap to the sample container, a sample sorting unit for sorting the sample containers by inspection groups, a chemical analyzer unit for automatically performing chemical analysis of the sample.

On the other hand, an automatic analyzing system having a rack transportation portion and a plurality of analyzing units is disclosed in Japanese Patent Application Laid-Open No.3-285175. In the automatic analyzing system, a sample is pipetted from a sample rack stopping on the rack transportation portion to an analyzer unit. The analyzer units are respectively connected to the rack transportation portion by a plurality of positioning pins.

In the above-mentioned systems disclosed in Hitachi Review, Vol.41, No.4 and Japanese Patent Application Laid-Open No.3-285175, a height adjusting mechanism is required independently in each of the treatment units such as analyzer units and the rack transportation portion. Further, it is necessary to perform height adjustment for each of the treatment units and the rack transportation portion with respect to a floor surface of a facility to install the system therein as the reference height level when the system is constructed.

If a treatment unit detachably combined with the rack transportation portion has a rack transferring area having an inlet port and an outlet port for the sample rack, the sample rack must be smoothly transferred from the rack transportation portion to the rack transferring area, and reversely from the rack transferring area to the rack transportation portion. However, it is not easy to make the levels of the inlet port and the outlet port for the sample rack installed at a comparatively high position from the floor surface agree with the level of the transportation surface of the rack transportation portion because there is unevenness on the floor surface to be used as the height level reference. That is, in order to prevent catching or falling of the sample rack when the sample rack is transferred between the rack transportation portion and the treatment unit, fine adjustment of the level is required and accordingly large labor is required in such adjusting work.

SUMMARY OF THE INVENTION

An object of the present invention is to provide a sample rack handling system in which work adjusting height level between a rack transportation assembly and a treatment unit structure can be performed with less labor in a construction in which the both are detachably combined, and a sample rack can be easily transferred between them.

The present invention is applied to a sample rack handling system which comprises a rack transportation assembly having a passage capable of transporting a sample rack holding a sample, the rack transportation assembly being installed on a floor surface; and a treatment unit structure having a rack transferring area for sending out and receiving the sample rack to and from the passage, the treatment unit structure being capable of being combined with the rack transportation assembly.

The rack transportation assembly comprises a projecting member formed in the rack transportation assembly below the passage, the projecting member projecting forward from the rack transportation assembly; a first reference surface facing upward formed on an upper surface of the projecting member; a plurality of adjusters for adjusting height, the adjuster being attached at a position lower than the projecting member in the rack transportation assembly.

Further, the treatment unit structure comprises a second reference surface facing downward formed at a position near a back surface of the treatment unit structure lower than the rack transferring area; casters to be used so as to contact to the floor surface when the treatment unit structure is moved on the floor surface, the casters being arranged at a position lower than the second reference surface in the treatment unit structure; and a height adjuster capable of adjusting a height from the floor surface in the front side of the treatment unit structure after the second reference surface is brought in contact with the first reference surface.

In a preferable embodiment of the present invention, the caster in the treatment unit structure is attached at a position where the caster does not come into contact with the rack transportation assembly when combining of the treatment unit structure with the rack transportation assembly is completed. Further, the rack transferring area in the treatment unit structure comprises a rack inlet port and a rack outlet port, and after completion of combining the treatment unit structure with the rack transportation assembly, a level of a rack transferring surface of the rack inlet port is equal to or lower than a level of a rack transportation surface of the passage in the rack transportation assembly, and a level of a rack transferring surface of the rack outlet port is equal to or higher than a level of a rack transportation surface of the passage in the rack transportation assembly, and a level difference between the rack transportation surface and each of the rack transferring surfaces does not exceed 5 mm.

Furthermore, in a preferable embodiment of the present invention, a plurality of treatment unit structures are combined with one rack transportation assembly. Further, the rack transportation assembly includes a rack having the projecting portion and the plurality of adjusters; and a rack transportation mechanism having the passage, the rack transportation mechanism being attached onto the rack. Further, the treatment unit structure comprises a plurality of vertical stripes formed in an equal interval on a front surface of the treatment unit structure, and a width dimension of the treatment unit structure is integer times of the interval of the stripes.

BRIEF DESCRIPTION OF DRAWINGS

FIG. 7A to FIG. 7F are schematic plan views explaining various examples of combination of rack transportation mechanism portions when the treatment unit structures are combined with one rack transportation assembly.

DESCRIPTION OF THE PREFERRED EMBODIMENTS

Initially, the total construction of an example of one layout in a sample rack handling system to which the present invention is applied will be conceptually described below, referring to FIG. 1.

Figure 1:
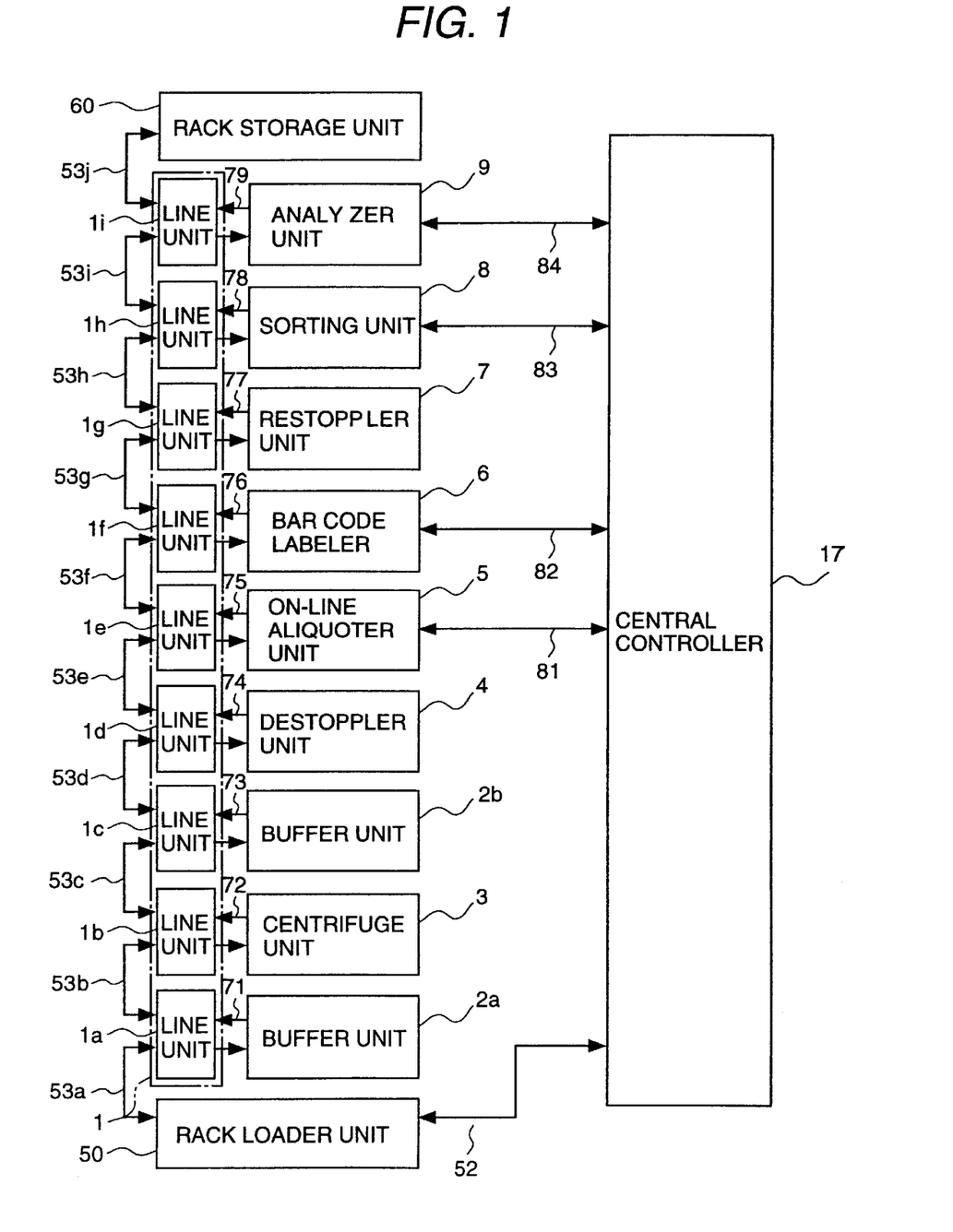
FIG. 1 is a block diagram conceptually showing an embodiment of layout in a sample rack handling system to which the present invention is applied.

The sample rack handling system of FIG. 1 comprises a rack transportation system 1 having a plurality of rack transportation line units 1a to 1i and a plurality of treatment units 2a, 2b, 3 to 9. Each of the line units 1a to 1i composes a rack transportation assembly to be described later. Each of the treatment units composes a treatment unit structure. Each of the treatment units is connected to the corresponding rack transportation assembly detachably, that is, separably from each other. A rack loader unit 50 is arranged in the start terminal side of the rack transportation system 1, and a rack storage unit 60 is arranged in the end terminal side of the rack transportation system 1. Each of buffer units 2a, 2b and the treatment units 3 to 9 respectively contains a unit control portion for controlling operation of its own unit, and has a function to transmit operation information of the its own unit to each of the partial line units 1a to 1i pairing with and corresponding to each of the treatment units. The centrifuge unit 3, the on-line aliquoter unit 5 and the analyzer unit 9 out of the plurality of treatment units 3 to 9 arranged along the rack transportation system 1 are units for performing physical treatments to a sample held in a sample rack. In addition, the analyzer unit 9 also performs chemical treatment on the extracted sample. On the other hand, the destoppler unit 4, the bar code labeler unit 6, the restoppler unit 7 and the sorting unit 8 are units for performing some operation to a container containing a sample. Here, these operations are generically called sample treatments. An off-line aliquoter unit may be arranged instead of the analyzer unit.

The rack loader unit 50, the rack storage unit 60 and the rack transportation system 1 composing the core portion in the sample rack handling system of FIG. 1 are connected to one another through communication cables 53a to 53j. The rack loader unit 50 controlling the core composing portion is connected to a central controller 17 through a communication cable 52. The buffer units 2a, 2b and the treatment units 3 to 9 are connected to the corresponding line units 1a to 1i forming pairs therewith through communication cables 71 to 79, respectively. Therefore, information on operation in connection with transportation of a sample rack in each treatment units is transmitted to the central controller through the line unit forming a pair.

Information on operating conditions regardless of transportation of a sample rack is communicated between the necessary treatment units and the central controller 17 through communication cables 81 to 84.

Each of the plurality of line units performs communication with the neighboring line units and communication with the treatment unit forming a pair and communication with the central controller 17. Dropping-in of a sample rack at a treatment unit is executed under control of the rack transportation system 1 by the central controller 17 when the central controller 17 confirms that the treatment unit can receive the sample rack. The on-line aliquoter unit 5 communicates with the central controller 17 on pipetting information. The bar code labeler unit 6 communicates with the central controller 17 on label printing information. Further, the sorting unit 8 communicates with the central controller 17 on sorting information, and the analyzer unit 9 communicates with the central controller 17 on pipetting and analyzing information.

A sample rack holding a general sample is set on the rack loader unit 50, and when inspection of an urgent sample is required, a sample rack holding the urgent sample is set on the rack loader unit. The sample rack set on the rack loader unit 50 is transported by the rack transportation system 1. In that case, the sample rack holding the urgent sample is transported in preference to the rack holding the general sample. When the transported rack arrives at a read portion, not shown, a rack kind (rack ID) and a sample identification number (sample ID) are read and registered in the central controller 17 for controlling the rack transportation system 1. The registered sample rack is further transported to be firstly stored in the buffer unit 2a if the rack is to be dropped in at the centrifuge unit 3. When the buffer unit 2a is fully filled with sample racks or when a preset time-out 10 period elapses, the sample racks are returned to the rack transportation system 1 from the buffer unit 2a to be successively transported into the centrifuge unit 3. The transported sample rack is centrifugal treatment performed for a preset time, and the sample rack after the treatment is returned to the rack transportation system 1.

A sample rack 10 (refer to FIG. 2) not dropped-in at the centrifuge unit 3 passes by the buffer unit 2a and the centrifuge unit 3. The buffer unit 2a is provided to make a sample rack to have centrifuge treatment performed next as a standby rack by completing treatment of the sample rack during centrifugal treatment of the preceding sample rack in order to improve speed of treatment.

A sample rack to be dropped in at the destoppler unit 4 is transported to the destoppler unit 4. In the centrifuge unit 3, loading and unloading are continuously performed because a predetermined number of sample racks are performed the buffer unit 2b is provided so as to prevent the sample racks from stagnating on the rack transportation system 1 during unloading them. In the destoppler unit 4, a cap of a sample test tube is opened, and the sample rack after completion of the destoppling treatment is returned to the rack transportation system 1. A sample rack 10 not dropping-in at the destoppler unit 4 passes by the destoppler unit 4.

A sample rack to be dropped in at the on-line aliquoter unit 5 is transported to the on-line aliquoter unit 5. In this unit, serum is sucked, and the serum in regard to only a sample requested by an instruction from the central controller 17 is pipetted into another container. After completion of pipetting, the sample rack is returned to the rack transportation system 1. On the other hand, the daughter sample rack formed by the pipetting is also transported by the rack transportation system 1. A sample rack not dropped in at the on-line aliquoter unit 5 passes by the on-line aliquoter unit 5.

A sample rack to be dropped in at the bar code labeler unit 6 is transported to the bar code labeler unit 6. Each of the test tubes held in the newly supplied daughter rack is labeled with the same sample identification number as that of the mother sample pipetted, and returned to the rack transportation system 1 after checking the label by reading. A sample rack 10 not dropped in at the bar code labeler unit 6 passes by the bar code labeler unit 6.

A sample rack to be dropped in at the restoppler unit 7 is transported to the restoppler unit 7. Each of the transported test tubes is stoppled, and the sample rack with the stoppling treatment performed thereon is returned to the rack transportation system 1. A sample rack not dropped in at the restoppler unit 7 passes by the restoppler unit 7.

A sample rack to be dropped in at the sorting unit 8 is transported to the sorting unit 8. Only a requested test tube out of the test tubes in the transported sample rack is transferred to and mounted on a designated position, and returned to the rack transportation system 1. A sample rack not dropped in at the sorting unit 8 passes by the sorting unit 8.

A sample rack 10 to be dropped in at the off-line aliquoter unit or the analyzer unit 9 is transported there. Only a requested sample is pipetted to a designated container, and returned to the rack transportation system 1 after completion of pipetting. A sample rack not dropped in at the off-line aliquoter unit or the analyzer unit 9 passes by there. Finally, the sample rack is transported to the rack storage unit 60.

Figure 2:
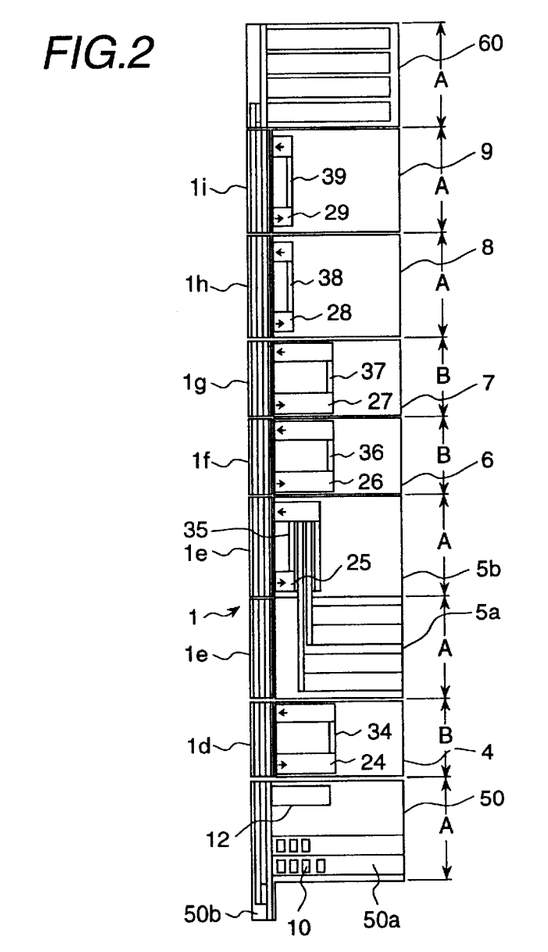
FIG. 2 is a view showing another embodiment of layout in a sample rack handling system to which the present invention is applied.

FIG. 2 is a view showing another embodiment of layout in a sample rack handling system. Portions having the same function as those in FIG. 1 are identified by the same reference characters. The treatment units in FIG. 2 are shown more concretely than those in FIG. 1. In comparison to the embodiment of the layout of FIG. 1, the embodiment of the layout of FIG. 2 does not have the buffer unit 2a, the centrifuge unit 3 and the buffer unit 2b. The rack loader unit 50 includes a rack loader unit 50a for a general sample, a rack loader unit 50b for an urgent sample and a reader unit 12 for reading rack ID bar codes and sample ID bar codes.

The treatment units 4 to 9 respectively have rack transferring areas 24 to 29 for transferring a sample rack 10 received from the rack transportation system. Each of the rack transferring areas has a rack inlet port and a rack outlet port. In FIG. 2, the rack inlet port and the rack outlet port are shown by arrows. In the destoppler unit 4, the sample rack received from the line unit 1d through the rack inlet port in the rack transferring area 24 is transferred to a destoppler position 34, and transferred to the rack outlet port in the rack transferring area 24 after removing the cap. Then, the sample rack is transferred to the line unit 1d through the rack outlet port. Such operation of transferring the sample rack from the rack inlet port to the rack outlet port through the treatment position is the same as operation in the other treatment units 5 to 9.

The on-line aliquoter unit 5 includes a supply unit 5a for supplying a daughter rack and an aliquot treatment unit 5b having a pipetter. In the aliquot treatment unit 5b, the rack entered into the rack transferring area 25 from the line unit 1e through the rack inlet port is transferred to the line unit 1e from the rack transferring area 25 though the rack outlet port after a sucking treatment is performed at a sample sucking position 35. In the bar code labeler unit 6, the rack entered into the rack transferring area 26 from the line unit 1f through the rack inlet port is transferred to the line unit 1f from the rack transferring area 26 though the rack outlet port after treatment is performed at a bar code labeling position 36.

In the restoppler unit 7, the rack entered into the rack transferring area 27 from the line unit 1g through the rack inlet port is transferred to the line unit 1g from the rack transferring area 27 though the rack outlet port after a restoppling treatment is performed at a position 37. In the sorting unit 8, the rack entered into the rack transferring area 28 from the line unit 1h through the rack inlet port is transferred to the line unit 1h from the rack transferring area 28 though the rack outlet port after an extracting treatment of a selected test tube at a position 38 is performed. In the analyzer unit 9, the rack entered into the rack transferring area 29 from the line unit 1i through the rack inlet port is transferred to the line unit 1i from the rack transferring area 29 though the rack outlet port after a sample sucking treatment of a selected test tube at a position 39 is performed.

Although each of the treatment units in the example shown in FIG. 2 has the rack inlet port and the rack outlet port arranged at positions different from each other, each of some units out of the plurality of treatment units may have a port commonly usable as the rack inlet port and the rack outlet port, if necessary. In the sample rack handling system as shown in FIG. 1 or FIG. 2, the order of arraying the treatment units may be changed and may be exchanged with each other. In addition, number of the treatment units may be increased or decreased.

Each of a treatment units 4 to 9 can transfer the sampling rack independently of each other in a state separated from the rack transportation system 1. The length in each of the treatment units along a direction transporting the sample rack on the rack transportation system 1 is standardized in two kinds or three kinds. In the example of FIG. 2, the width of each of the treatment unit is either 450 mm or 600 mm. As the concept of the system, this dimension is integer times of a spacing of vertical stripes, to be described later, uniformly spaced and arranged on a front surface of the total system after constructing the system along the transporting direction of the sample rack. That is, the spacing of the stripes is 150 mm.

In the sample rack handling system shown in FIG. 1 or FIG. 2, the rack loader unit 50 and the rack storage unit 60 are integrated with the rack transportation system 1 before each of the treatment unit structures are combined. The rack transportation system integrated with the rack loader unit and the rack storage unit as described above is sometimes called a core structure portion.

The relationship of relative height between the rack transportation assembly and the treatment unit structure will be described below, referring to FIG. 3. It is possible to construct it such that one treatment unit structure is combined with one rack transportation assembly. However, it is preferable that a plurality of treatment unit structures are combined with one rack transportation assembly, as described later referring to FIG. 7.

Figure 3:
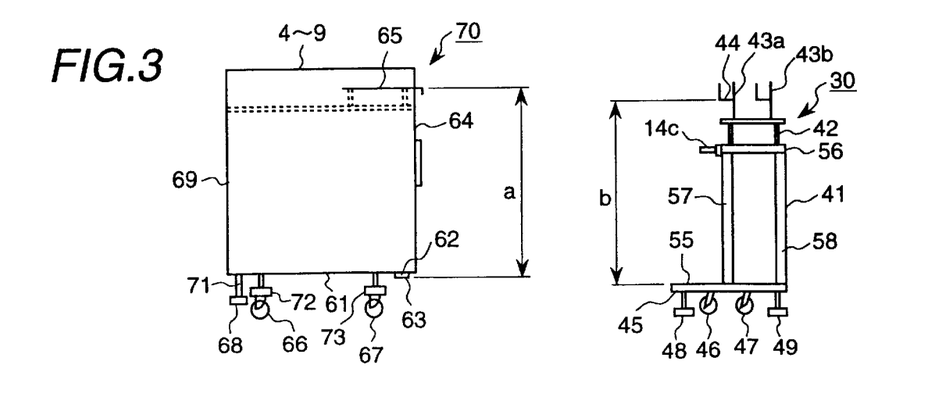
FIG. 3 is a schematic side view explaining the level relationship between the rack transportation assembly and the treatment unit structure.

Referring to FIG. 3, the rack transportation assembly 30 comprises a rack transportation mechanism 42 and a platform 41. The frame of the platform 41 includes a projecting member 45 composed of a parallelepiped box or L-shaped metal members and plates, upper end frames 56 and a plurality of columns 57, 58 connecting them. A positioning pin 14c is attached to the front side of the upper end frame 56. The projecting member 45 also serves as a base of the platform 41. The projecting member 45 is projected toward the front of the rack transportation assembly 30 so as to mount a part of the treatment unit structure 70. The length of the portion of the projecting member 45 projecting frontward from the support 57 is longer than the length of the positioning pin 14c.

A plurality of casters 46, 47 and a plurality of adjusters 48, 49 are attached onto the bottom surface of the projecting member 45. It is preferable that both the number of the casters and the number of the adjusters are four or more. When the rack transportation assembly 30 is moved on a floor of an inspection room, rollers of the casters 46, 47 rotate in contact when the floor to make the movement of the rack transportation assembly 30 smooth. When the rack transportation assembly 30 is moved, the adjusters 48, 49 are drawn back toward the projecting member 45 side so that the lower ends of the adjusters are positioned at a level higher than that of the lower ends of the casters 46, 47. The adjusters 48, 49 are used for adjusting height when the rack transportation assembly 30 is fixed on the floor after the set position is determined. The adjusters 48, 49 can be extended so that the lower ends of the casters 46, 47 are out of contact with the floor.

The projecting member 45 is constructed in such a shape that the top surface in the portion projecting frontward from the support 57 forms a rectangular area having the long sides along the width direction of the platform 41. The top surface of the area in the projecting member 45 is polished flat and smooth. The flat-and-smooth surface is a first reference surface 55. That is, the first reference surface 55 the height direction is formed in facing upward.

A rack transportation mechanism 42 is attached onto the upper end frame 56 of the platform 41. The rack transportation mechanism 42 comprises a passage 43a for a rack supply line, a passage 43b for rack return line, a conveyer belt capable of mounting and transferring the sample rack and a motor for driving the conveyer belt. Since the surface of the conveyer belt stretched in the passage 43a is in contact with the bottom surface of the sample rack, the belt surface servers as a rack transportation surface 44. In a case where the sample rack is transported using a means for transporting the sample rack without using any belt, that is, the rack is transported using a hook reciprocally movable along the passage 43a, the rack is moved in sliding fashion on a bottom surface of the passage 43a which becomes the rack transportation surface. The treatment unit structure 70 corresponding to each of the various kinds of treatment units 4 to 9 (refer to FIG. 2) has the rack transferring area, as described above. On the rack transferring area, the sample rack is moved using a movable hook or a rack pushing mechanism. In this case, the surface of the rack transferring area becomes the rack transferring surface 65. One or more projections 62 having a smoothly polished surface are provided on the bottom surface 61 of the box-shaped treatment unit structure 70. The projection 62 is formed at a position nearer to the back surface of the treatment unit structure 70 than an attached position of the caster 67. In a case of providing a plurality of the projections 62, the projections are arranged along and nearly parallel to a ridgeline in the lower end of the back surface 64. The smooth bottom surface on the projection 62 becomes a second reference surface in the height direction. That is the second reference surface is formed facing downward.

The plurality of casters 66, 67 and the plurality of adjusters 68 are attached on the bottom surface 61 of the treatment unit structure 70. The number of the casters 66, 67 in one treatment unit structure 70 is preferably three or more. The number of the adjusters 68 in one treatment unit structure 70 is two or more. The plurality of adjusters 68 are arranged along and nearly parallel to a lower ridgeline in the front surface 69 of the treatment unit structure 70.

When the treatment unit structure 70 is moved on the floor in the inspection room, the lower ends of the adjusters 68 do not contact the floor surface because the adjusters 68 are drawn back toward the bottom surface 61 by height adjusting screws 71. However, the rollers in the lower ends of the casters 66, 67 are in contact with the floor surface to make the movement of the treatment unit structure smooth by the rotation of the rollers. The lower ends of the adjusters 68 and the lower ends of the casters 66, 67 are nearer to the floor surface than the reference surface. The adjusters 68 are provided at positions nearer to the lower edge of the front surface 69 than positions of the casters 66. The casters 66, 67 are capable of being raised or lowered using height adjusters 72, 73.

The procedure of setting the treatment unit structure 70 to the rack transportation assembly 30 will be described below, referring to FIG. 4A, FIG. 4B and FIG. 4C. The rack transportation assembly 30 transported into the inspection room is moved to a set position by the function of the casters 46, 47. By lowering the lower ends of the plurality of adjusters 48, 49 lower than the lower ends of the casters 46, 47, the lower ends of the adjusters are brought contact with the floor surface. At that time, the height of the rack transportation assembly 30 is adjusted by the adjusters 48, 49 so that the rack transportation assembly becomes horizontal in both the front-and-back direction and the right-and-left direction.

Figure 4A:
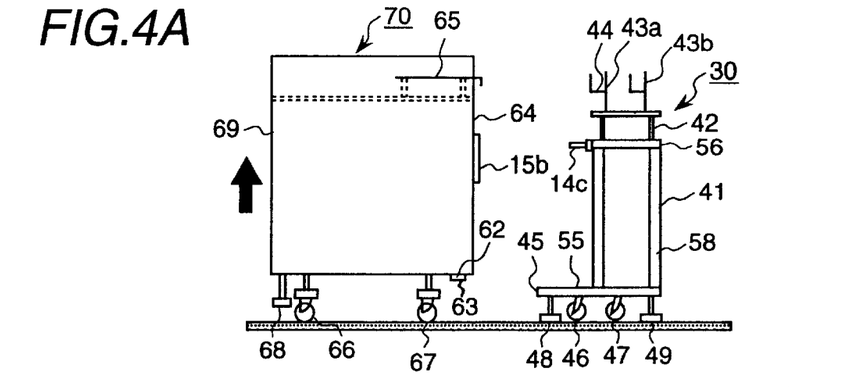
FIG. 4A, FIG. 4B and FIG. 4C are views explaining the process when the treatment unit structure is combined with the rack transportation assembly.
Figure 4B:
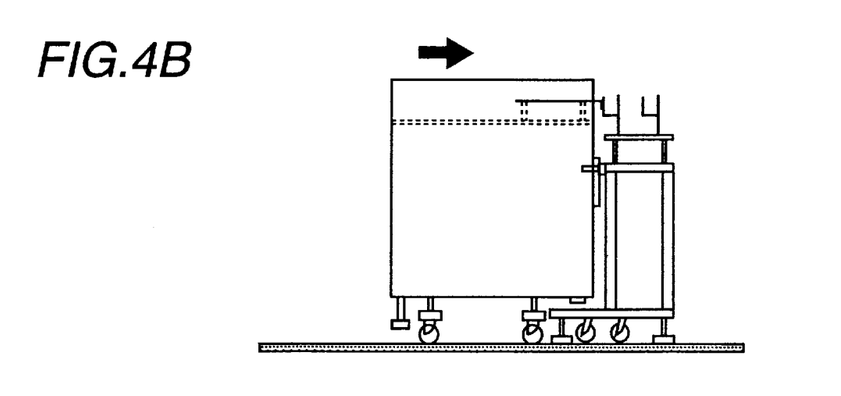

On the other hand, the treatment unit structure 70 moved near the front surface side of the rack transportation assembly 30 by the function of the casters 66, 67 is lifted by operation of the height adjusters 72, 73 of the casters 66, 67 so that the reference surface 63 of the projection 62 facing downward becomes higher than the reference surface 55 of the projecting member 45 facing upward, as shown in FIG. 4A. Then, as shown in FIG. 4B, the back surface 64 of the treatment unit structure 70 is set opposite to the front surface of the rack transportation assembly 30 having been fixed, and the treatment unit structure 70 is pushed toward the rack transportation assembly 30 from the front surface 69 side of the treatment unit structure 70, and the positioning pin 14c is inserted into a vertically long groove in a plate 15b.

Figure 4C:
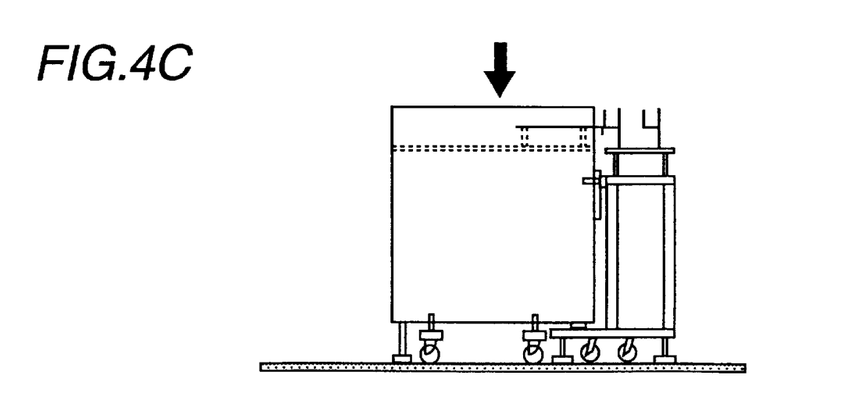

After that, as shown in FIG. 4C, the treatment unit structure 70 is lowered by operation of the height adjusters of the casters 66, 67 in the treatment unit structure 70. When the lower surface of the projection 62 is brought in contact with the upper surface of the projecting member 45, the height adjusting work by the height adjusters of the casters 66, 67 is stopped. By doing so, the first reference surface 55 agrees with or contacts the second reference surface 63.

After that, the height adjusting screws of the adjusters 68 are operated so that the height in the front surface 69 side agrees with the height in the back surface 64 side and at the same time the lower ends of the plurality of adjusters 68 arranged on the right hand side and on the left hand side in the width direction are brought in contact with the floor surface. The attaching position of the caster 67 attached onto the lower surface 61 is determined so that the caster 67 nearer to the back surface 64 is not in contact with the projecting member 45 when the setting is completed as shown in FIG. 4C.

The relative relationship between a height dimension a (refer to FIG. 3) between the reference surface 63 of the projection 62 and the rack transferring surface 65 in the treatment unit structure 70 and a height dimension b (refer to FIG. 3) between the reference surface 55 of the projecting member 45 and the rack transportation surface 44 in the rack transportation assembly 30 is kept constant. By doing so, the height adjusting work in order to make transferring of the sample rack smooth becomes easy. In FIG. 4B and FIG. 4C, the reference characters are omitted for the sake of simplification.

When the rack transportation assembly 30 and the treatment unit structure 70 are combined with or connected to each other, special consideration is paid so as to make transportation or transferring of the sample rack smooth after completion of the setting. That is, in a case where the inlet port and the outlet port for receiving and sending out the sample rack are separately arranged in each of the treatment unit structures, a relationship expressed by the following equations (1) and (2) exists between the dimension b between the reference surface 55 of the projecting member 45 and the rack transportation surface 44 in the rack transportation assembly 30 and the dimension a between the reference surface 63 of the projection 62 and the rack transferring surface (the surface of the inlet port and the outlet port in each of the treatment units which the rack bottom surface is in contact with) 65 in the treatment unit structure 70.

$$a \leq b \leq a+5 \text{ mm} \quad (1)$$

$$b \leq a \leq b+5 \text{ mm} \quad (2)$$

The equation (1) corresponds to an equation applied to the case where the sample rack is moved (carried in) from the passage 43a in the rack transportation assembly 30 to the inlet port of the rack transferring area in the treatment unit structure 70, and the equation (2) corresponds to an equation applied to the case where the sample rack is moved (carried out) from the outlet port of the rack transferring area in the treatment unit structure 70 to the passage 43a in the rack transportation assembly 30. The equation (1) means that the level of the rack transportation surface 44 is equal to or higher than the level of the rack transferring surface 65 at the inlet, but the level difference does not exceed 5 mm. The condition of b being equal to or larger than a means that if on the contrary, b is smaller than a, an ascending step in the moving direction of the sample rack is formed and accordingly the sample rack may be caught in that portion. This disturbs smooth moving or transporting of the sample rack, and in addition the sample held in the sample rack may be scattered. The condition of b being equal to or smaller than (a+5 mm) means that if b exceeds the value (a+5 mm), a large step is formed at that portion to possibly cause falling or scattering of the sample. The equation (2) means that the level of the rack transferring surface 65 at the outlet is equal to or higher than the level of the rack transportation surface 44, but the level difference does not exceed 5 mm. The reason is the same as in the case of the equation (1).

Figure 5:
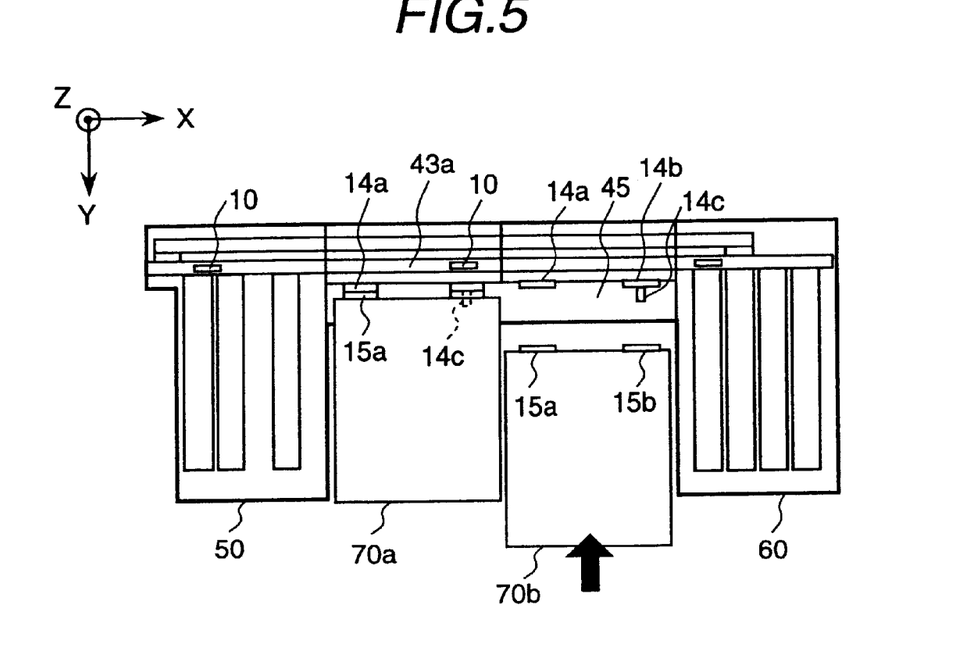
FIG. 5 is a view explaining positioning in a width direction and in a depth direction when the treatment unit structures are combined with the rack transportation assembly.

FIG. 5 is a schematic plan view explaining positioning in a width direction and in a depth direction when two of the treatment unit structures 70a, 70b are combined with the one rack transportation assembly 30. In FIG. 5, the Z-axis is taken in the height direction, the X-axis is taken in the width direction along the passage 43a which intersects with the height direction at a right angle, and the Y-axis is taken in the depth direction which intersects with both of the height direction and the width direction at right angle. Only two treatment unit structures are shown in FIG. 5 because the positioning can be performed in a similar way even if the number and the kinds of the treatment unit structures are changed.

Referring to FIG. 5, the rack transportation assembly 30 comprises plates 14a and 14b respectively having a positioning reference surface, and the plate 14b has a pin 14c for positioning in the X-direction. Each of the treatment unit structures 70a, 70b comprises plates 15a and 15b respectively having a positioning reference surface in the Y-direction. The plate 15b has a vertical long groove in the Z-direction, and by inserting the positioning pin 14c in the groove the surface of the plate 14b and the surface of the plate 15b are brought in contact with each other to perform positioning in the X-direction.

By pushing the treatment unit structure 70b in the direction shown by an arrow in FIG. 5 at setting the treatment unit structure to the rack transportation assembly, the plates 15a and the 15b are respectively brought in contact with the plates 14a and 14b to make the positioning reference surfaces agree with each other and to make the pin 14c engaged into the vertical long groove. This state can be understood by referring to the connected state shown by the treatment unit structure 70a. Thereby, positioning of the rack transportation assembly and each of the treatment unit structures in the X-direction and the Y-direction in connection with the transported sample rack 10 is automatically performed, and consequently adjustment-free setting in these direction can be realized.

It is preferable that a relative positioning error in the X-direction and the Y-direction between the rack transportation assembly and the treatment unit structure is below 5 mm. By doing so, the sample rack can be smoothly moved or transported, and falling of the sample rack and scattering of the sample can be prevented.

Figure 6:
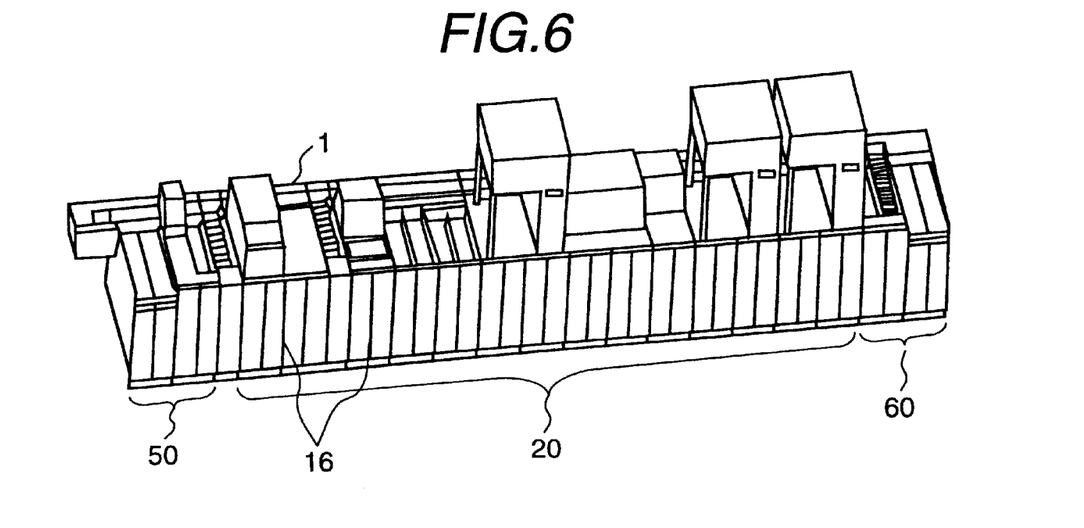
FIG. 6 is an outward view showing a further embodiment of layout in a sample rack handling system to which the present invention is applied.

FIG. 6 is an outward view showing a further embodiment of layout in a sample rack handling system to which the present invention is applied. A plurality of treatment unit structures are tightly arranged between the rack loader unit 50 and the rack storage unit 60. In FIG. 6, a cluster composed of a plurality of treatment unit structures is indicated by the reference character 20. The rack transportation system 1 is arranged along the back surface of the cluster 20.

Vertical stripes 16 composed of slits uniformly spaced in the direction along the direction transporting the sample rack in the rack transportation system 1 are provided on each of the front surfaces of the plurality of treatment unit structures composing the cluster 20. A length of the sample rack in the direction along the direction transporting the sample rack is 120 mm, and a length of a tray in the sample rack receiving side and a tray in the sample rack sending side in the direction (width) along the direction transporting the sample rack is generally 150 mm. This dimension is set to a minimum unit, and the spacing of the vertical stripes 16 is set to 150 mm by matching with the minimum dimensional unit. A width of each of the treatment unit structure is set to a value integer times of the stripe spacing. This is because it is possible, by doing so, to obtain a designing effect capable of expressing that the system is a continuous body of the treatment units.

FIG. 7A to FIG. 7F are schematic plan views explaining various examples of a combination of rack transportation mechanism portions when a plurality of the treatment unit structures 70 are combined with one rack transportation assembly 30. As the racks for the one rack transportation assembly 30, three kinds of platforms, that is, a rack 41*a* of 1050 mm width, a rack 41*b* of 1200 mm width and a platform 41*c* of 1650 mm width are prepared. As the rack transportation mechanisms to be set to the platform, two kinds of rack transportation mechanisms 42*a* and 42*b* having a length agreeing with the width of the treatment unit structure 70 to be attached to the rack are prepared. These rack transportation mechanisms correspond to the line units 1*a* to 1*i* in FIG. 1 and FIG. 2. The length of the rack transportation mechanism 42*a* is 450 mm, and the length of the rack transportation mechanism 42*b* is 600 mm.

Figure 7A:
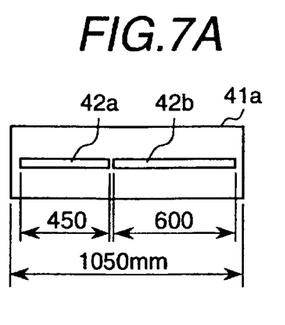
Figure 7B:
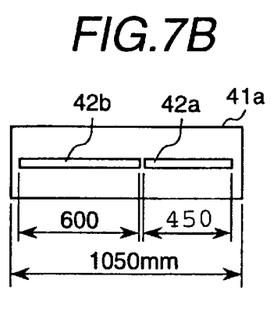
Figure 7C:
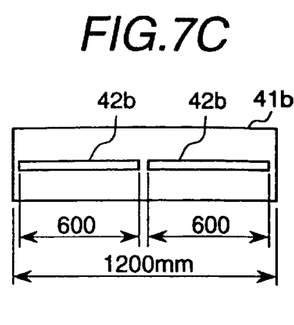
Figure 7D:
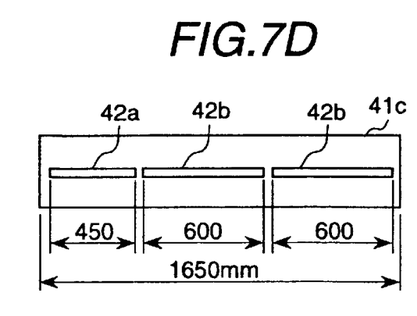
Figure 7E:
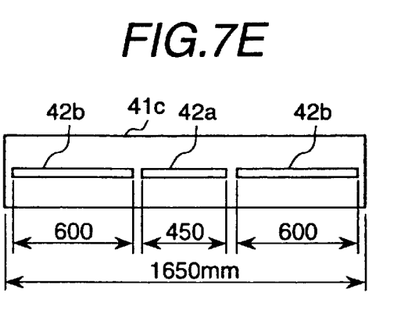
Figure 7F:
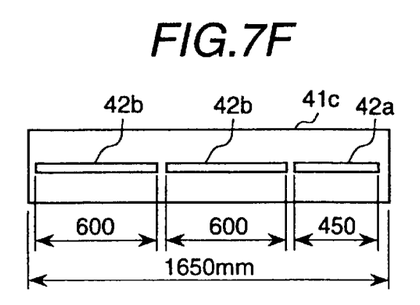

FIG. 7A to FIG. 7C show examples of attaching two rack transportation mechanisms to one platform, and FIG. 7D to FIG. 7F show examples of attaching three transportation mechanisms to one platform. The treatment unit 4, 6 or 7 of 450 mm width is attached on the front surface side of the rack transportation mechanism 42*a* of 450 mm length, and the treatment unit 5*a*, 5*b*, 8 or 9 of 600 mm width is attached on the front surface side of the rack transportation mechanism 42*b* of 600 mm length. Either of the rack transportation mechanisms has a length, that is, a length of the passage 43*a* or 43*b* equal to integer times of the minimum dimensional unit 150 mm. The rack transportation assembly in each example of the FIG. 7A to FIG. 7F is used solely or in a combined and connected state so as to be inserted between the rack loader unit 50 and the rack storage unit 60.

As having described above, according to the present invention, it is possible to substantially reduce manpower for height adjusting work when the treatment unit structure is detachably set to the rack transportation assembly, and in spite of reducing the manpower it is possible to smoothly transfer the sample rack between the treatment unit structure and the rack transportation assembly.

What is claimed is:

1. A sample rack handling system comprising a rack transportation assembly having a passage capable of transporting a sample rack holding a sample, the rack transportation assembly being supported on a floor surface; and a treatment unit structure having a rack transferring area for sending out and receiving the sample rack to and from said passage, the treatment unit structure being detachably combined with said rack transportation assembly so that the sample rack is transferred from one of said rack transferring area and said passage to the other of said rack transferring area and said passageway, which further comprises:

a projecting member formed on said rack transportation assembly below said passage, the projecting member projecting forward from said rack transportation assembly;

a first reference surface facing upwardly formed on an upper surface of said projecting member;

a plurality of adjusters for adjusting the height of said rack transportation assembly, the adjusters being attached at a position lower than said projecting member on said rack transportation assembly;

a second reference surface mounted on said treatment unit structure and facing downwardly and located at a position near a back surface of said treatment unit structure which is lower than said rack transferring area of said treatment unit structure;

casters for contacting said floor surface when said treatment unit structure is moved on the floor surface, said casters being arranged at a position which is lower than said second surface on said treatment unit structure; and a height adjuster for adjusting a height from the floor surface of said treatment unit structure after said downwardly facing second reference surface of said treatment unit structure is brought into contact with said upwardly facing first reference surface of said projecting member of said rack transportation assembly; and wherein said rack transferring area comprises a rack inlet port and a rack outlet port, and after completion of combining said treatment unit structure with said rack transportation assembly, a level of a rack transferring surface of said rack inlet port is not higher than a level of a rack transportation surface of said passage in said rack transportation assembly, a level of a rack transferring surface of said rack outlet port is not lower than a level of a rack transportation surface of said passage in said rack transportation assembly, and a level difference between said rack transportation surface and each of said rack transferring surfaces being not larger than 5 mm.

2. A sample rack handling system according to claim 1 wherein said treatment unit structure comprises a plurality of vertical stripes formed in equal intervals on a front surface of said treatment unit structure, and a width dimension of said treatment unit structure is integer times the interval of said stripes.

\* \* \* \* \*